(12) United States Patent
Birkbeck

(10) Patent No.: US 9,273,268 B2
(45) Date of Patent: Mar. 1, 2016

(54) WOODY ODORANTS

(71) Applicant: FIRMENICH SA, Geneva (CH)

(72) Inventor: Anthony A. Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 57 days.

(21) Appl. No.: 14/367,496

(22) PCT Filed: Dec. 20, 2012

(86) PCT No.: PCT/EP2012/076257
§ 371 (c)(1),
(2) Date: Jun. 20, 2014

(87) PCT Pub. No.: WO2013/092781
PCT Pub. Date: Jun. 27, 2013

(65) Prior Publication Data
US 2015/0005214 A1    Jan. 1, 2015

(30) Foreign Application Priority Data
Dec. 21, 2011 (EP) .................................... 11194756

(51) Int. Cl.
| | | |
|---|---|---|
| *C11D 3/50* | (2006.01) | |
| *C11B 9/00* | (2006.01) | |
| *C07C 49/553* | (2006.01) | |
| *A61K 8/35* | (2006.01) | |
| *A61Q 13/00* | (2006.01) | |

(52) U.S. Cl.
CPC ................. *C11B 9/0042* (2013.01); *A61K 8/35* (2013.01); *A61Q 13/00* (2013.01); *C07C 49/553* (2013.01); *C11D 3/50* (2013.01); *C07C 2103/66* (2013.01)

(58) Field of Classification Search
CPC ..................................................... C07C 49/553
USPC ....................................................... 568/373
See application file for complete search history.

(56) References Cited

U.S. PATENT DOCUMENTS

| | | | |
|---|---|---|---|
| 3,929,677 A | | 12/1975 | Hall et al. |
| 3,967,629 A | * | 7/1976 | Chappell et al. ............... 131/276 |
| 3,968,070 A | * | 7/1976 | Sundt ............................. 549/332 |
| 3,979,338 A | * | 9/1976 | Sundt ............................... 512/13 |
| 5,538,944 A | | 7/1996 | Fankhauser et al. |

FOREIGN PATENT DOCUMENTS

| | | |
|---|---|---|
| EP | 678497 B1 | 1/1998 |
| GB | 2164644 A | 3/1986 |

OTHER PUBLICATIONS

International Search Report and Written Opinion, application No. PCT/EP2012/076257, mailed Feb. 20, 2013.
Lee et al., J. Am. Chem. Soc., 125:5839-5848 (2003).
Alder et al., Chem. Ber., 88(3): 407-419 (1955).

* cited by examiner

*Primary Examiner* — John Hardee
(74) *Attorney, Agent, or Firm* — Winston & Strawn LLP

(57) ABSTRACT

The present invention concerns compounds of formula (I) in the form of any one of its stereoisomers or a mixture thereof, and wherein one dotted line represents a carbon-carbon single or double bond and the others a carbon-carbon single bond; each R, independently from each other, represents a hydrogen atom or a methyl or ethyl group provided that at least one of said R groups represents a methyl or ethyl group; and $R^1$ represents a methyl or ethyl group; and their use in perfumery to impart odor notes of the woody type having cedar, ambery, patchouli and/or rooty aspect.

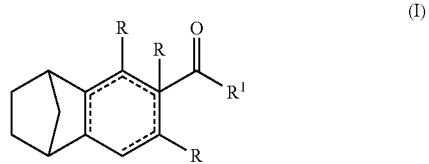

13 Claims, No Drawings

WOODY ODORANTS

TECHNICAL FIELD

The present invention relates to the field of perfumery. More particularly, it concerns compounds of formula (I), as defined below, which are useful perfuming ingredients of the woody, ambery/cedar type. The present invention concerns also the invention's compounds as part of a perfuming composition or of a perfuming consumer product.

PRIOR ART

To the best of our knowledge, the invention's compounds of formula (I) are novel.

To the best of our knowledge, the closest analogues known in the perfumery are the ones described in U.S. Pat. No. 3,929,677. However, although the invention's compounds possess odor profiles having some similarity with the ones of the prior art compounds, they differ from the latter by having a significantly different chemical structure. This prior art document does not report or suggest any organoleptic properties of the compounds of formula (I) and does not report or suggest any use of said compounds in the field of perfumery.

DESCRIPTION OF THE INVENTION

We have now surprisingly discovered that a compound of formula

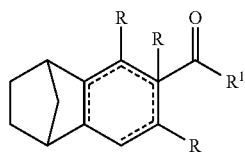

(I)

in the form of any one of its stereoisomers or a mixture thereof, and wherein one dotted line represents a carbon-carbon single or double bond and the others a carbon-carbon single bond;

each R, independently from each other, represents a hydrogen atom or a methyl or ethyl group provided that at least one of said R groups represent a methyl or ethyl group; and $R^1$ represents a methyl or ethyl group;

can be used as perfuming ingredient, for instance to impart odor notes of the woody type.

The odor of the family is here described as woody, but it is intended that the various compounds do have various shades of the woody family. These shades may include cedar, ambery, patchouli and/or rooty aspect.

For the sake of clarity, by the expression "wherein one dotted line represents a carbon-carbon single or double bond and the others a carbon-carbon single bond", or the similar, it is meant the normal meaning understood by a person skilled in the art, i.e. that the whole bonding (solid and dotted lines) between the carbon atoms connected by said dotted line is a carbon-carbon single or double bond.

According to a particular embodiment of the invention, at least one of said R groups represents a methyl or ethyl group and at least one of said R groups represents a hydrogen atom.

According to any one of the above embodiments of the invention, two of said R groups represent a methyl or ethyl group and one of said R groups represents a hydrogen atom.

According to any one of the above embodiments of the invention, $R^1$ represents a methyl group.

According to any one of the above embodiments of the invention, said compounds (I) are $C_{14}$-$C_{15}$ compounds.

According to any one of the above embodiments of the invention, said compound (I) is a compound wherein one dotted line represents a carbon-carbon double bond and the others a carbon-carbon single bond.

According to any one of the above embodiments of the invention, said compound (I) is a compound wherein carbon atom 4a is a $sp^2$ carbon, i.e. the dotted lines between carbon atoms 4a and 8a, or between 4a and 5, represent a carbon-carbon double bond. In such a case, said compound (I) can be of formula

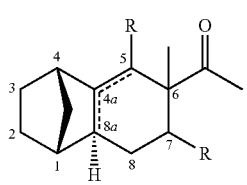

(II)

wherein the dotted lines and R have the same meaning as above. According to a particular embodiment of formula (II), one of said R represents a hydrogen and the other R represents a methyl or ethyl group.

For the sake of clarity, by the expression "any one of its stereoisomers", or the similar, it is meant the normal meaning understood by a person skilled in the art, i.e. that the invention's compound can be a pure enantiomer (if chiral) or diastereomer.

According to any one of the above embodiments of the invention, in the case where the carbon atoms 4a and 8a are $sp^3$ carbons, said compound possesses a relative stereochemistry according to formula

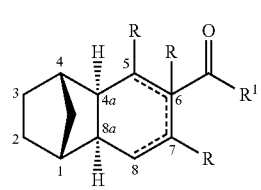

(II')

wherein the dotted lines, R and $R^1$ have the same meaning as above.

The compounds of formula (I) are new compounds, and therefore also an object of the present invention.

As specific examples of the invention's compounds, one may cite, as non-limiting example, 1-[(1RS,4SR)-1,2,3,4,5,6,7,8-octahydro-6,7-dimethyl-1,4-methanonaphthalen-6-yl]-ethanone which possesses an odor characterized by a woody, cedar/ambery note with a sweet, floral aspect. The woody note reminds surprisingly of Iso E® Super (1-(octahydro-2,3,8,8-tetramethyl-2-naphthalenyl)-1-ethanone), origin: International Flavors & Fragrances, USA), but differentiates from the latter by having a grapefruit under-note and having also a stronger rooty/vetiver connotation.

As other example, one may cite 1-[(1RS,4SR,8aSR)-1,2,3,4,6,7,8,8a-octahydro-5,6-dimethyl-1,4-methanonaphthalen-6-yl]-ethanone which possesses a woody, ambrinol, patchouli and earthy character with cedar/vetiver notes, also reminding surprisingly of Iso E® Super, with a vetiver and iris aspect.

As other specific, but non-limiting, examples of the invention's compounds, one may cite the following ones in Table 1:

TABLE 1

Invention's compounds and their odor properties

| Compound structure and name | Odor notes |
|---|---|
| 1-[(1RS,4SR,4aSR,8aSR)-5,7-dimethyl-1,2,3,4,4a,5,6,8a-octahydro-1,4-methanonaphthalen-6-yl]ethanone | Woody, ambery/cedar, reminding of Iso E ® Super |
| 1-[(1RS,4SR,4aSR,5SR,6RS,8aSR)-5,7-dimethyl-1,2,3,4,4a,5,6,8a-octahydro-1,4-methanonaphthalen-6-yl]ethanone | Woody, cedar, incense and slightly patchouli notes. More incense than the above 1-[(1RS,4SR,4aSR,8aSR)-5,7-dimethyl-1,2,3,4,4a,5,6,8a-octahydro-1,4-methanonaphthalen-6-yl]ethanone |
| 1-[(1RS,4SR,4aRS,8aSR)-7-methyldecahydro-1,4-methanonaphthalen-6-yl]ethanone | Woody, ambery/cedar, jasmonic notes with earthy, cedar bottom notes |
| 1-((1RS,4SR,4aRS,8aSR)-7-methyl-1,2,3,4,4a,5,6,8a-octahydro-1,4-methanonaphthalen-6-yl)-1-propanone | Woody, cedar, powdery odor |
| 1-((1RS,4SR,4aRS,8aSR)-7-methyl-1,2,3,4,4a,5,6,8a-octahydro-1,4-methanonaphthalen-6-yl)ethanone | Woody, ambery/cedar, earthy notes |

According to a particular embodiment of the invention, the compounds of formula (I) are 1-[(1RS,4SR)-1,2,3,4,5,6,7,8-octahydro-6,7-dimethyl-1,4-methanonaphthalen-6-yl]-ethanone, 1-[(1RS,4SR,8aSR)-1,2,3,4,6,7,8,8a-octahydro-5,6-dimethyl-1,4-methanonaphthalen-6-yl]-ethanone or 1-[(1RS,4SR,4aSR,5SR,6RS,8aSR)-5,7-dimethyl-1,2,3,4,4a,5,6,8a-octahydro-1,4-methanonaphthalen-6-yl]ethanone.

Surprisingly, the invention's compounds do have odor notes reminding of those of Iso E® Super, although they do have also specific organoleptic differences. This odor similarity is striking since the chemical structure of the invention's compounds and of Iso E® Super is quite different especially on the methyl substitution of the decaline ring.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono-, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 60% by weight, or even more, of the compounds of the invention based on the weight of the composition into which they are incorporated. Concentrations lower than these, such as in the order of 0.001% to 20% by weight, can be used when these compounds are incorporated into perfumed articles, percentage being relative to the weight of the article.

The invention's compounds can be prepared from 2-norbornene according to a method as described in Scheme 1:

Scheme 1: General synthetic pathway

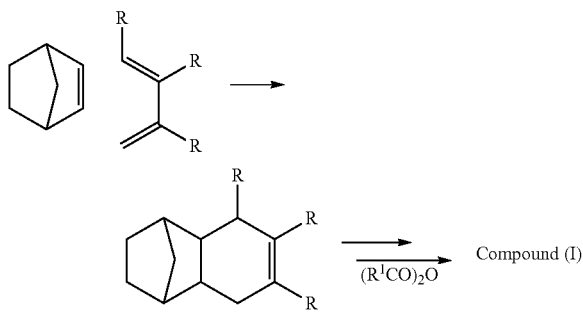

wherein R and $R^1$ have the meaning indicated above. The reaction pathway may include a step wherein the double bond of the first intermediate is isomerized in other positions. The Examples herein below show different examples of such approach.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

2,3-Dimethylenebicyclo[2.2.1]heptane was prepared according to *Chem. Ber.*, 1955, 88, 407 or *J. Am. Chem. Soc.*, 2003, 125, 5839. 4-Methyl-tricyclo[6.2.1.0(2,7)]undec-4-ene was obtained as described in EP 678497.

Example 1

Synthesis of Compounds of Formula (I)

A)

Diels Alder General Procedure with 2,3-dimethylenebicyclo[2.2.1]heptane

The dienophile (17 mmol) was dissolved in $CH_2Cl_2$ (25 mL) and cooled to −30° C. in an ice bath. $EtAlCl_2$ (1.0 M in hexanes, 8.32 mL, 8.32 mmol, 0.5 eq) was added slowly dropwise. The solution was stirred at 0° C. for a further 5-10 minutes then the 2,3-dimethylenebicyclo[2.2.1]heptane (2.0 g, 17 mmol) was added slowly dropwise. The reaction mixture was allowed to slowly warm to ambient temperature and stirred for a further 1-2 hours at ambient temperature, then poured into water and ether. Vigorously stirred for 30 minutes, then the aqueous phase was re extracted with ether. The combined organic phase was washed with $NH_4Cl$, then $NaHCO_3$, then brine, dried over sodium sulfate, then filtered and the solvents removed in vacuo to yield the crude product. Further purification by column chromatography and or bulb to bulb distillation gave the desired product.

Preparation of 1-[(1RS,4SR)-1,2,3,4,5,6,7,8-octahydro-6,7-dimethyl-1,4-methanonaphthalen-6-yl]-ethanone dienophile: 3-Me-pent-3-en-2-one.

Bulb to bulb distillation 150° C. at 0.1 mbar gave the desired ketone X as a colorless oil, 2.0 g, mixture of isomers (endo:exo 9:1, plus 1:1 methyl epimers) and 56% yield.

$^{13}C$ NMR: 214.3, 214.0, 138.1, 137.3, 136.7, 136.4, 51.4, 51.38 (q), 46.9, 46.4 ($CH_2$), 45.1, 44.9, 44.88, 44.77, 34.3 (CH), 33.2 ($CH_2$), 32.9 (CH), 29.6, 29.2, 26.14, 26.1, 25.8, 25.7 ($CH_2$), 25.3, 25.2, 16.2, 16.0 ($CH_3$).

B)

Diels Alder General Procedure with Norbornene and Dienes

In a stainless steel autoclave norbornene (1 eq) was dissolved in the diene (1.0-1.6 eq) and BHT (di-tert butyl hydroxytoluene) then sealed and the mixture was heated at 180° C. in an oil bath for 24-48 hrs. The mixture was cooled, then the residue was distilled under vacuum to yield the desired alkene.

a) (1RS,2RS,3RS,7RS)-3,5-dimethyl-tricyclo[6.2.1.0 (2,7)]undec-4-ene and (1RS,2RS,3SR,7RS)-3,5-dimethyl-tricyclo[6.2.1.0(2,7)]undec-4-ene (minor)

Norbornene (50.0 g, 0.53 mol), methyl penta-1,3-diene (65.4 g, 0.79 mol) and BHT (0.3 g) (48 hrs) gave after fractional distillation (0.08 mbar at 80° C.) the desired alkene, 65.0 g (1:4, isomers).

$^{13}C$ NMR: Major isomer: 135.9 (q), 128.3 (CH), 52.3, 44.2, 43.0, 41.2, (CH), 33.7, 33.6 ($CH_2$), 32.6 (CH), 30.1, 29.7 ($CH_2$), 23.2, 21.0 ($CH_3$).

b) (1RS,2SR,7RS,8SR)-3,4-dimethyltricyclo[6.2.1.0 (2,7)]undec-4-ene

Norbornene (11.5 g, 121 mmol), 3-methyl penta-1,3-diene (15.0 g, 182 mmol) and BHT (0.3 g) (48 hrs) gave after fractional distillation (0.04 mbar at 100° C.) the desired alkene, 8.7 g (1:4, isomers).

$^{13}C$ NMR: Major isomer: 139.7 (q), 122.1 (CH), 52.5, 43.7, 43.4, 41.6, (CH), 33.7 ($CH_2$), 35.1 (CH), 30.2, 29.6 ($CH_2$), 28.2 ($CH_2$), 20.4, 17.4 ($CH_3$).

Isomerisation General Procedure

The bridged alkene (100 mmol) was dissolved in ethanol (50 mL) and palladized charcoal (10% Pd/C, 1.0 g) was added and the suspension was heated under reflux for 1-4 hrs then cooled. The suspension was filtered and the solvents removed in vacuo to yield the crude alkene. Further purification by bulb to bulb distillation under vacuum and or column chromatography gave the desired alkene. (80-90% yield).

a) (1RS,4SR,4aRS,8aSR)-5,7-dimethyl-1,2,3,4,4a,5,6,8a-octahydro-1,4-methanonaphthalene $^{13}C$ NMR: Major isomer: 135.0 (q), 124.8 (CH), 50.0, 44.1, 42.9, 40.6, (CH), 36.9, 33.6 ($CH_2$), 33.0 (CH), 29.9, 29.3 ($CH_2$), 24.0, 21.9 ($CH_3$).

b) (1RS,2SR,7RS,8SR)-3,4-dimethyltricyclo[6.2.1.0 (2,7)]undec-3-ene $^{13}$C NMR: 128.3, 127.7 (q), 49.3, 43.3, 41.8, 41.3 (CH), 34.2, 30.5, 29.8, 29.6, 27.2 (CH$_2$), 20.3, 17.8, (CH$_3$).

Acylation Procedures

Preparation of 1-[(1RS,4SR,4aSR,8aSR)-5,7-dimethyl-1,2,3,4,4a,5,6,8a-octahydro-1,4-methanonaphthalen-6-yl]ethanone Zinc chloride (5.0 g, 36 mol %) was fused under vacuum then cooled under nitrogen with stirring. The alkene obtained in B)a) (75 mmol) and the acid anhydride (35 g, 350 mmol) in either ClCH$_2$CH$_2$Cl (100 mL) or toluene (50 mL) was added and then the suspension heated at 80-90° C. for 2-3 hours then cooled. The mixture was portioned between water and ether, then re-extracted with ether. The organic phase was washed with water, then NH$_4$Cl, NaHCO$_3$, brine then dried over MgSO$_4$, filtered and the solvents removed in vacuo to yield the crude ketone. Further purification by bulb to bulb distillation and or column chromatography gave the desired ketone. (50-80% yield).

Bulb to bulb distillation at 0.1 mbar at 110° C. gave the desired ketone as a mixture of isomers (14:10:6:54), 12.2 g.

$^{13}$C NMR: Major isomer 212.5, 131.5 (q), 128.3 (CH), 59.2, 48.6, 43.7, 42.7, 40.6, 35.5 (CH), 33.6 (CH$_2$), 29.8 (CH$_3$), 30.1, 29.0 (CH$_2$), 21.2, 20.0 (CH$_3$).

Preparation of 1-[(1RS,4SR,8aSR)-1,2,3,4,6,7,8,8a-octahydro-5,6-dimethyl-1,4-methanonaphthalen-6-yl]-ethanone A solution of EtAlCl$_2$ (1.0 M in hexanes, 3.1 mL, 3.1 mmol) was added slowly dropwise to a stirred solution of (1RS,2SR,7RS,8SR)-3,4-dimethyltricyclo[6.2.1.0(2,7)]undec-3-ene obtained in (1.0 g, 3.1 mmol) in CH$_2$Cl$_2$ (10 mL) cooled to 5° C. at such a rate that the temperature remained <5° C. The reaction mixture was allowed to warm slowly to ambient temperature over 1 hour then poured into a mixture of ice/water. The mixture was re-extracted with ether twice, washed with water, NaHCO$_3$ then brine, dried over Na$_2$SO$_4$, filtered and the solvents removed in vacuo to yield the crude ketone, 1.2 g as a pale yellow oil. Further purification by chromatography (80 G cartridge Puriflash PF50-SiHP) with cyclohexane:ethyl acetate, 19:1, then 9:1, then 4:1, gave the desired ketone, which was bulb to bulb distilled 160° C. at 0.2 mbar, to give the ketone 600 mg as a mixture of isomers (72:28).

$^{13}$C NMR: Major isomer 213.5, 146.4, 120.4 54.5 (q), 45.4, 40.8, 40.4 (CH), 37.0, 33.8, 31.2, 25.8, (CH$_2$), 24.7 (CH$_3$), 24.2 (CH$_2$), 21.7, 15.5 (CH$_3$).

Preparation of 1-((1RS,4SR,4aRS,8aSR)-7-methyl-1, 2,3,4,4a,5,6,8a-octahydro-1,4-methanonaphthalen-6-yl)ethanone ZnBr$_2$ (3.0 g, 13.4 mmol) was added to a solution of acetic anhydride (30 mL) and 4-methyl-tricyclo[6.2.1.0(2,7)]undec-4-ene (10.0 g, 62 mmol) and then heated under reflux. After 2 hours at reflux the mixture was cooled then poured into dilute NH$_4$OH (6%) and extracted with diethyl ether. The organic phase was washed with saturated NaHCO$_3$, then brine, dried over Na$_2$SO$_4$, filtered and the solvents removed in vacuo. The crude ketone (9.3 g orange oil) was further puri-fied by bulb to bulb distillation 0.1 mbar at 120° C. gave the desired ketone, 5.4 g as a mixture of isomers (7:6:16:21:16).

After chromatography cartridge (40 G silica gel) with cyclohexane:ethyl acetate as eluent gave the desired isomer. Further purification by bulb to bulb distillation 0.3 mbar at 130° C. gave the alpha isomer as a mixture of endo and exo epimers, (91:4), 450 mg.

$^{13}$C NMR: desired isomer 209.6 (q), 132.9 (q), 128.5 (CH), 53.4 (CH), 43.2, 43.0, 41.9, 38.5 (CH), 32.9, 30.7, 29.6, 28.9 (CH$_2$), 28.7, 24.0 (CH$_3$).

Further elution gave the beta isomer, further purification by bulb to bulb distillation 0.3 mbar at 130° C. gave the beta isomer (α-β unsaturation) 700 mg.

$^{13}$C NMR: Beta isomer 201.4 (q), 147.4 (q), 134.5 (q), 43.5, 42.7, 42.5, (CH), 37.6, 33.0, 29.9 (CH$_3$), 29.7, 29.6 (CH$_2$), 22.0 (CH$_3$).

Preparation of 1-((1RS,4SR,4aRS,8aSR)-7-methyl-1, 2,3,4,4a,5,6,8a-octahydro-1,4-methanonaphthalen-6-yl)-1-propanone ZnBr$_2$ (3.5 g, 15.4 mmol) was suspended in dichloroethane (15 mL) and heated to reflux. A solution of propionic anhydride (12.0 g, 92 mmol) and 4-methyl-tricyclo[6.2.1.0(2,7)] undec-4-ene (5.0 g, 30.8 mmol) in dichloroethane (10 mL) was added slowly dropwise. After 6 hours at reflux the mixture was cooled then poured into dilute NH4OH (6%) and extracted with diethyl ether. The organic phase was washed with saturated NaHCO$_3$, then brine, dried over Na$_2$SO$_4$, filtered and the solvents removed in vacuo. The crude ketone (8.0 g orange oil) was further purified by bulb to bulb distillation 0.2 mbar at 120° C. gave the desired ketone, 3.2 g (48%) as a mixture of isomers (21:25:22:12).

$^{13}$C (100 MHz) (mixture of isomers): 214.2, 213.8, 212.1, 204.8 (q), (159.8, 158.2 (q), ENOL ester), 149.0, 146.2 (q), 133.5, 133.0, 132.9, (q), 128.5, 128.2, 124.7, 118.4 (CH), 55.6, 52.5, 51.0, 46.1, 43.8, 43.6, 43.4, 43.2, 43.1, 43.0, 42.9, 42.7, 42.5, 42.2, 42.1, 41.9, 40.7 (CH), 38.6, 37.6, 37.3, 35.8, 34.6, 34.4, 34.0, 33.5, 33.2, 33.0, 32.9, 31.6, 31.2, 30.9, 30.0, 29.8, 29.6, 29.6, 29.5, 28.9, 28.8, 28.6, 28.4, 27.8 (CH$_2$), 24.0, 21.8, 21.1, 20.9, 14.5, 14.3, 7.8, 7.7 (CH$_3$).

MS: m/z (+) 218.

General Epimerization Procedure

A solution of sodium ethoxide (21% in ethanol, 0.5 mL) was added slowly dropwise to a solution of the ketone mixture (1 g, xx mmol) in ether (5 mL) at ambient temperature. The mixture was stirred at ambient temperature for a further 12-15 hrs then poured into water and ether. The aqueous phase was re-extracted with ether. The combined organic phase was washed with saturated NH$_4$Cl, brine, then dried over Na$_2$SO$_4$, filtered and the solvents removed in vacuo to yield the crude ketone. Further purification by bulb to bulb distillation under reduced pressure gave the desired ketone as a different mixture of isomers.

Preparation of 1-[(1RS,4SR,4aSR,5SR,6RS,8aSR)-5, 7-dimethyl-, 2,3,4,4a,5,6,8a-octahydro-1,4-methanonaphthalen-6-yl]ethanone Sodium ethoxide (21% in Ethanol, 0.5 mL) was added to a stirred solution of 1-[(1RS,4SR,4aSR,8aSR)-5,7-dimethyl-1, 2,3,4,4a,5,6,8a-octahydro-1,4-methanonaphthalen-6-yl] ethanone (0.9 g, 4.6 mmol) in ether (5 mL) and left to stir at ambient temperature for 12 hrs. Added acetic acid (1 mL) and ether, then washed the organic phase with water 2×, then brine, dried over Na2SO4, filtered and the solvents removed in vacuo to yield the crude ketone, 0.75 g. Bulb to bulb distillation at 0.2 mbar, 110° C. gave the desired ketone as a mixture of isomers (46:6:18:23).

$^{13}$C NMR: major isomer 210.3, 132.7 (q), 128.6 (CH), 60.2, 46.6, 44.8, 42.8, 40.5, 35.6 (CH), 33.4 (CH$_2$), 30.8 (CH$_3$), 29.6, 29.2 (CH$_2$), 23.5, 19.2 (CH$_3$).

General Hydrogenation Procedure

In a stainless steel autoclave, the ketone (10 mmol) was dissolved in ethyl acetate (10 mL) and Pd/C (10%, 100 mg) was added and the suspension was purged 5 times with hydrogen gas, then stirred under an atmosphere of hydrogen gas (5-10 bar) for 1-3 hours. Excess hydrogen pressure was then vented and purged with nitrogen then filtered through a plug of silica and the plug washed with ethyl acetate. The solvents removed in vacuo. Bulb to bulb distillation of the residue gave the desired ketone, 80-95%.

Preparation of 1-[(1RS,4SR,4aRS,8aSR)-7-methyl-decahydro-1,4-methanonaphthalen-6-yl]ethanone $^{13}$C NMR: 211.9 (q), 55.5, 42.9, 42.1, 37.3 (CH), 32.8, 30.3, 29.8, 29.6, 27.6 (CH$_2$), 26.8 (CH), 28.6, 22.5 (CH$_3$).

Example 2

Preparation of a Perfuming Composition

A perfuming composition, of the woody type, was prepared by admixing the following ingredients:

| Parts by weight | Ingredient |
|---|---|
| 20 | Ambrox ® [1)] |
| 20 | Anethol |
| 50 | 10%* Angelica oil |
| 20 | Cashmeran ® [2)] |
| 400 | 8-Methoxy-2,6,6,8-tetramethyl-tricyclo[5.3.1.0(1,5)]undecane |
| 20 | Lemon essential oil |
| 20 | Coranol ™ [3)] |
| 650 | 70%** Galaxolide ® [4)] |
| 250 | Hedione ® [5)] |
| 20 | Orange essential oil |
| 50 | Sclareolate ® [6)] |
| 30 | 10%* Terpineol |
| 80 | Vetyver oil |
| 370 | Vetyverol |
| 2000 | |

*in dipropyleneglycol
**in isopropyle myristate
[1)](−)-(8R)-8,12-epoxy-13,14,15,16-tetranorlabdane; origin: Firmenich SA, Geneva, Switzerland
[2)]1,2,3,5,6,7-hexahydro-1,1,2,3,3-pentamethyl-4-indenone; origin: International Flavors & Fragrances, USA
[3)]4-cyclohexyl-2-methyl-2-butanol; origin: Firmenich SA, Geneva, Switzerland
[4)]1,3,4,6,7,8-hexahydro-4,6,6,7,8,8-hexamethyl-cyclopenta-g-2-benzopyrane; origin: International Flavors & Fragrances, USA
[5)]methyl dihydrojasmonate; origin: Firmenich SA, Geneva, Switzerland
[6)]propyl (S)-2-(1,1-dimethylpropoxy)propanoate; origin: Firmenich SA, Geneva, Switzerland The addition of 200 parts by weight of 1-[(1RS,8SR)-4,5-dimethyl-tricyclo[6.2.1.0(2,7)]undec-2(7)-en-4-yl]ethanone to the above-described composition twisted the latter from a woody note to a woody, sweet (almost vanilla) note and reinforced the vetiver notes.

The addition of the same amount of Iso E® Super (1-(octahydro-2,3,8,8-tetramethyl-2-naphthalenyl)-1-ethanone) to the above-described composition reinforced the ambery notes while the vetiver notes were not modified.

Example 3

Preparation of a Perfuming Composition

A perfuming composition for a detergent, of the floral type, was prepared by admixing the following ingredients:

| Parts by weight | Ingredient |
|---|---|
| 10 | Benzyl acetate |
| 120 | Verdyl acetate |
| 100 | Hexylcinnamic aldehyde |
| 20 | Methyl anthranilate |
| 50 | 1%* Ethyl 2-methyl-pentanoate |
| 25 | 10%* Methyl benzoate |
| 30 | Benzylacetone |
| 20 | Boisambrene ® [1)] |
| 50 | 10%* 2-Ethoxynaphthalene |
| 25 | Cetalox ® [2)] |
| 5 | Citronellyl nitrile |
| 40 | (1'R,E)-2-ethyl-4-(2',2',3'-trimethyl-3'-cyclopenten-1'-yl)-2-buten-1-ol |
| 120 | Dihydromyrcenol |
| 20 | Exaltolide ® [3)] Total |
| 10 | 10%* 2-Methyl-4-(2,2,3-trimethyl-3-cyclopenten-1-yl)-4-penten-1-ol |
| 20 | 10%* Ethyl tricyclo[5.2.1.0.(2,6)]decane-2-carboxylate |
| 10 | Ionone Alpha |
| 10 | Ionone Beta |
| 20 | Lilial ® [4)] |
| 130 | Linalol |
| 20 | 10%* Methylisoeugenol |
| 130 | Verdyl propionate |
| 40 | Isobornyl propionate |
| 50 | 10%* Romascone ® [5)] |
| 50 | Rose Centifolia essential oil |
| 150 | Tetrahydromyrcenol |
| 10 | Gamma undecalactone |
| 25 | Undecavertol |
| 420 | Verdox ® [6)] |
| 20 | 10%* (2,2-Dimethoxyethyl)benzene |
| 50 | 10%* 2,4-Dimethyl-3-cyclohexene-1-carbaldehyde |
| 1800 | |

*in dipropyleneglycol
[1)](methoxymethoxy)cyclododecane; origin: Symrise, Holzminden, DE
[2)]dodecahydro-3a,6,6,9a-tetramethyl-naphtho[2,1-b]furan; origin: Firmenich SA, Geneva, Switzerland
[3)]pentadecanolide; origin: Firmenich SA, Geneva, Switzerland
[4)]3-(4-tert-butylphenyl)-2-methylpropanal; origin: Givaudan SA, Vernier, Switzerland
[5)]methyl 2,2-dimethyl-6-methylene-1-cyclohexanecarboxylate; origin: Firmenich SA, Geneva, Switzerland
[6)]2-tert-butyl-1-cyclohexyl acetate; origin: International Flavors & Fragrances, USA The addition of 200 parts by weight of 1-[(1RS,8SR)-4,5-dimethyl-tricyclo[6.2.1.0(2,7)]undec-2(7)-en-4-yl]ethanone to the above-described composition imparted to the latter a warm woody note, slightly cedar and with an elegant grapefruit bottom note and imparted also a rooty twist.

By the addition of the same amount of Iso E® Super (1-(octahydro-2,3,8,8-tetramethyl-2-naphthalenyl)-1-ethanone) to the above-described composition, the effect was drier, more ambery and not at all citrusy.

Example 4

Preparation of a Perfuming Composition

A perfuming composition for a softener, of the floral, musky and powdery type, was prepared by admixing the following ingredients:

| Parts by weight | Ingredient |
| --- | --- |
| 25 | Benzyl acetate |
| 60 | Linalyl acetate |
| 70 | Verdyl acetate |
| 20 | 10%* Acetophenone |
| 40 | Anisic aldehyde |
| 20 | Aldehyde C 12 |
| 450 | Hexylcinnamic aldehyde |
| 10 | Allyl amyl glycolate |
| 20 | Methyl anthranilate |
| 10 | Cetalox ® [1] |
| 30 | Ethyle cinnamate |
| 30 | Citronellol |
| 70 | Coumarine |
| 5 | Damascenone |
| 20 | Dartanol |
| 40 | Decal |
| 15 | Ethylpraline |
| 450 | Ethylvanilline |
| 5 | Eugenol F |
| 5 | 3-(4-Methoxyphenyl)-2-methylpropanal |
| 150 | Hedione ® [2] |
| 120 | 1,3-Benzodioxole-5-carbaldehyde |
| 5 | Isoeugenol |
| 100 | Alpha iso methylionone |
| 280 | Lilial ® [3] |
| 180 | Linalol |
| 100 | Lyral ® [4] |
| 15 | Ethyl 2,3-epoxy-3-phenylbutanoate |
| 200 | Muscenone ® [5] Delta |
| 65 | Gamma nonalactone |
| 10 | Patchouli oil |
| 30 | Phenethylol |
| 50 | Orange essential oil |
| 10 | Prunella ® [6] |
| 300 | Romandolide ® [7] |
| 50 | Rose Wardia essential oil |
| 90 | Hexyl salicylate |
| 150 | Sandela ® [8] |
| 20 | Tamarine Base[6] |
| 10 | Terpineol |
| 40 | Gamma undecalactone |
| 60 | Vanilline |
| 70 | Verdox |
| 3500 | |

* in dipropyleneglycol
** in isopropyle myristate
[1] dodecahydro-3a,6,6,9a-tetramethyl-naphtho[2,1-b]furan; origin: Firmenich SA, Geneva, Switzerland
[2] methyl dihydrojasmonate; origin: Firmenich SA, Geneva, Switzerland
[3] 3-(4-tert-butylphenyl)-2-methylpropanal; origin: Givaudan SA, Vernier, Switzerland
[4] 4/3-(4-hydroxy-4-methylpentyl)-3-cyclohexene-1-carbaldehyde; origin: International Flavors & Fragrances, USA
[5] 3-methyl-5-cyclopentadecen-1-one; origin: Firmenich SA, Geneva, Switzerland
[6] compounded perfumery base; origin: Firmenich SA, Geneva, Switzerland
[7] (1S,1'R)-[1-(3',3'-dimethyl-1'-cyclohexyl)ethoxycarbonyl]methyl propanoate; origin: Firmenich SA, Geneva, Switzerland
[8] 5-(2,2,3-trimethyl-3-cyclopentenyl)-3-methylpentan-2-ol; origin: Firmenich SA, Geneva, Switzerland
[9] 2-tert-butyl-1-cyclohexyl acetate; origin: International Flavors & Fragrances, USA The addition of 500 parts by weight of 1-[(1RS,8SR)-4,5-dimethyl-tricyclo[6.2.1.0(2,7)]undec-2(7)-en-4-yl]ethanone to the above-described composition imparted to the latter a sweetness and functional aspect.

By the addition of the same amount of Iso E® Super (1-(octahydro-2,3,8,8-tetramethyl-2-naphthalenyl)-1-ethanone) to the above-described composition, the effect was drier, less sweet, more cedar and less functional.

Example 5

Preparation of a Perfuming Composition

A perfuming composition for a masculine cologne, of the woody type, was prepared by admixing the following ingredients:

| Parts by weight | Ingredient |
| --- | --- |
| 40 | Linalyl acetate |
| 20 | 10% * Myrcenyl acetate |
| 20 | Ambrox Super ® [1] |
| 20 | Anethol |
| 50 | 10% *Angelica roots oil |
| 20 | Cashmeran ® [2] |
| 400 | Cedramber[3] |
| 50 | Lemon essential oil |
| 600 | 70% ** Galaxolide ® [4] |
| 250 | Hedione ® [5] |
| 50 | Linalool |
| 20 | Orange essential oil |
| 10 | Terpineol |
| 80 | Vetyver essential oil |
| 370 | Vetyverol |
| 2000 | |

* in dipropyleneglycol
** in isopropyle myristate
[1] (−)-(8R)-8,12-epoxy-13,14,15,16-tetranorlabdane; origin: Firmenich SA, Geneva, Switzerland
[2] 1,2,3,5,6,7-hexahydro-1,1,2,3,3-pentamethyl-4-indenone; origin: International Flavors & Fragrances, USA
[3] 8-Methoxy-2,6,6,8-tetramethyl-tricyclo[5.3.1.0(1,5)]undecane
[4] 1,3,4,6,7,8-hexahydro-4,6,6,7,8,8-hexamethyl-cyclopenta-g-2-benzopyrane; origin: International Flavors & Fragrances, USA
[5] methyl dihydrojasmonate; origin: Firmenich SA, Geneva, Switzerland The addition of 2000 parts by weight of 1-[(1RS,4SR,8aSR)-1,2,3,4,6,7,8,8a-octahydro-5,6-dimethyl-1,4-methanonaphthalen-6-yl]-ethanone to the above-described composition imparted to the latter a woody note, rather patchouli and very soft.

By the addition of the same amount of Iso E® Super (1-(octahydro-2,3,8,8-tetramethyl-2-naphthalenyl)-1-ethanone) or Vertofix (1-(2,6,8,8-, tetramethyl tricyclo(5.3.1.01,5)undec-8-en-9-yl)-1-ethanone) to the above-described composition, the effect was drier and more dry cedar.

1-[(1RS,4SR,8aSR)-1,2,3,4,6,7,8,8a-octahydro-5,6-dimethyl-1,4-methanonaphthalen-6-yl]-ethanone reinforced the vetiver note whereas Iso E® Super and Vertofix emphasize to a dry-amber note.

Example 6

Preparation of a Perfuming Composition

A perfuming composition for a cologne, of the musky and citrus type, was prepared by admixing the following ingredients:

| Parts by weight | Ingredient |
| --- | --- |
| 360 | Linalyl acetate |
| 20 | 10% * Ambrinol |
| 30 | Ambrox Super ® [1] |
| 600 | Lemon essential oil |
| 60 | Coumarin |
| 50 | 10% *Damascone Alpha |
| 700 | Dihydromyrcenol |
| 20 | Estragon |
| 40 | 10% * Farenal[2] |
| 10 | 2-Methyl-4-(2,2,3-trimethyl-3-cyclopenten-1-yl)-4-penten-1-ol |
| 200 | 70%** Galaxolide ® [3] |
| 30 | Geraniol |
| 120 | Geranium oil |
| 350 | Hedione ® [4] |
| 10 | Laurier Noble |
| 150 | Linalool |
| 80 | Lyral ® [5] |

| Parts by weight | Ingredient |
| --- | --- |
| 10 | Norlimbanol Dextro[6] |
| 140 | 7-Methoxy-3,7-dimethyl-2-octanol |
| 500 | Tonalide ® [7] |
| 20 | Vanilline |
| 3500 | |

* in dipropyleneglycol
** in isopropyle myristate
[1](−)-(8R)-8,12-epoxy-13,14,15,16-tetranorlabdane; origin: Firmenich SA, Geneva, Switzerland
[2]2,6,10-trimethyl-9-undecenal; origin: Symrise, Holzminden, DE
[3]1,3,4,6,7,8-hexahydro-4,6,6,7,8,8-hexamethyl-cyclopenta-g-2-benzopyrane; origin: International Flavors & Fragrances, USA
[4]methyl dihydrojasmonate; origin: Firmenich SA, Geneva, Switzerland
[5]4/3-(4-hydroxy-4-methylpentyl)-3-cyclohexene-1-carbaldehyde; origin: International Flavors & Fragrances, USA
[6]trans-1-(2,2,6-trimethyl-1-cyclohexyl)-3-hexanol; origin: Firmenich SA, Geneva, Switzerland
[7](5,6,7,8-tetrahydro-3,5,5,6,8,8-hexamethyl-2-naphthyl)-1-ethanone; origin: Givaudan SA, Vernier, Switzerland The addition of 1500 parts by weight of 1-[(1RS,4SR,8aSR)-1,2,3,4,6,7,8,8a-octahydro-5,6-dimethyl-1,4-methanonaphthalen-6-yl]-ethanone to the above-described composition imparted to the latter a woody, warm/tropical aspect unknown in the palette and which could not be achieved with any known ingredient, even when used at such high percentage. This effect demonstrates its ease of use and versatility, because the effect is different compared to the first composition.

Example 7

Preparation of a Perfuming Composition

A perfuming composition for detergent, of the floral and woody type, was prepared by admixing the following ingredients:

| Parts by weight | Ingredient |
| --- | --- |
| 250 | Verdyl acetate |
| 200 | Hexylcinnamic aldehyde |
| 40 | Methyl anthranilate |
| 40 | 10% * Applinate[1] |
| 60 | Benzylacetone |
| 50 | Cetalox ® [2] |
| 20 | Citronellyl Nitrile |
| 80 | Dartanol[3] |
| 250 | Dihydromyrcenol |
| 90 | Exaltolide Total ® [4] |
| 40 | 10% * 2-Methyl-4-(2,2,3-trimethyl-3-cyclopenten-1-yl)-4-penten-1-ol |
| 50 | 10% * Ethyl tricyclo[5.2.1.0.(2,6)]decane-2-carboxylate |
| 20 | Ionone Alpha |
| 10 | Ionone Beta |
| 20 | Iralia ® [5] |
| 100 | Lilial[6] |
| 260 | Linalool |
| 50 | 10% * Methylisoeugenol |
| 260 | Verdy propionate |
| 80 | Isobornyl propionate |
| 120 | 10% * Romascone ® [7] |
| 100 | Rose Wardia oil |
| 300 | Tetrahydromyrcenol |
| 50 | 10% * 2,4-Dimethyl-3-cyclohexene-1-carbaldehyde |
| 20 | Gamma undecalactone |
| 50 | Undecavertol |
| 800 | Verdox ® [8] |

| Parts by weight | Ingredient |
| --- | --- |
| 50 | 10% * (2,2-Dimethoxyethyl)benzene |
| 40 | Ylang oil |
| 3500 | |

* in dipropyleneglycol
[1]ethyl 2-methyl-pentanoate; origin: Firmenich SA, Geneva, Switzerland
[2]dodecahydro-3a,6,6,9a-tetramethyl-naphtho[2,1-b]furan; origin: Firmenich SA, Geneva, Switzerland
[3](1'R,E)-2-ethyl-4-(2',2',3'-trimethyl-3'-cyclopenten-1'-yl)-2-buten-1-ol; origin: Firmenich SA, Geneva, Switzerland
[4]pentadecanolide; origin: Firmenich SA, Geneva, Switzerland
[5]mixture of methylionones isomers: Firmenich SA, Geneva, Switzerland
[6]3-(4-tert-butylphenyl)-2-methylpropanal; origin: Givaudan SA, Vernier, Switzerland
[7]methyl 2,2-dimethyl-6-methylene-1-cyclohexanecarboxylate; origin: Firmenich SA, Geneva, Switzerland
[8]2-tert-butyl-1-cyclohexyl acetate; origin: International Flavors & Fragrances, USA The addition of 1500 parts by weight of 1-[(1RS,4SR,8aSR)-1,2,3,4,6,7,8,8a-octahydro-5,6-dimethyl-1,4-methanonaphthalen-6-yl]-ethanone to the above-described composition imparted to the latter a soft and smooth woody aspect. This note is also observed on the wet and dry fabric.

What is claimed is:

1. A compound of formula

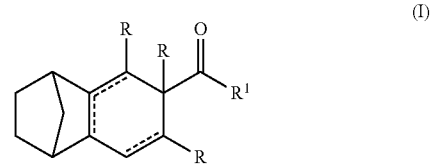

(I)

in the form of any one of its stereoisomers or a mixture thereof, and wherein one dotted line represents a carbon-carbon single or double bond and the others a carbon-carbon single bond;
each R, independently from each other, represents a hydrogen atom or a methyl or ethyl group provided that at least one of said R groups represents a methyl or ethyl group; and
$R^1$ represents a methyl or ethyl group.

2. A compound according to claim 1, wherein two of said R groups represent a methyl or ethyl group and one of said R groups represents a hydrogen atom.

3. A compound according to claim 2, wherein one dotted line represents a carbon-carbon double bond and the others a carbon-carbon single bond.

4. A compound according claim 2, wherein the dotted line between carbon atoms 4a and 8a, or between 4a and 5, represents a carbon-carbon double bond.

5. A compound according to claim 1, wherein one dotted line represents a carbon-carbon double bond and the others a carbon-carbon single bond.

6. A compound according claim 5, wherein the dotted line between carbon atoms 4a and 8a, or between 4a and 5, represents a carbon-carbon double bond.

7. A compound according to claim 1, wherein the dotted line between carbon atoms 4a and 8a, or between 4a and 5, represents a carbon-carbon double bond.

8. A compound according to claim 1, wherein said compound (I) is 1-[(1RS,4SR)-1,2,3,4,5,6,7,8-octahydro-6,7-dimethyl-1,4-methanonaphthalen-6-yl]-ethanone, 1-[(1RS,4SR,8aSR)-1,2,3,4,6,7,8,8a-octahydro-5,6-dimethyl-1,4-methanonaphthalen-6-yl]-ethanone, 1-[(1RS,4SR,4aSR, 8aSR)-5,7-dimethyl-1,2,3,4,4a,5,6,8a-octahydro-1,4-methanonaphthalen-6-yl]ethanone, 1-[(1RS,4SR,4aSR,5SR,6RS,8aSR)-5,7-dimethyl-1,2,3,4,4a,5,6,8a-octahydro-1,4-methanonaphthalen-6-yl]ethanone, or 1-[(1RS,4SR,4aRS,8aSR)-7-methyldecahydro-1,4-methanonaphthalen-6-yl]ethanone.

9. A method to confer, enhance, improve or modify the odor properties of a perfuming composition or of a perfumed article, which method comprises adding to said composition or article an effective amount of at least a compound of formula (I)

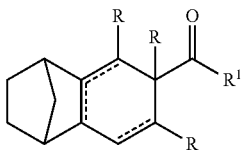

(I)

in the form of any one of its stereoisomers or a mixture thereof, and wherein one dotted line represents a carbon-carbon single or double bond and the others a carbon-carbon single bond;
each R, independently from each other, represents a hydrogen atom or a methyl or ethyl group provided that at least one of said R groups represents a methyl or ethyl group; and
$R^1$ represents a methyl or ethyl group.

10. A perfuming composition comprising
i) at least one compound of formula (I):

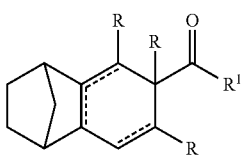

(I)

in the form of any one of its stereoisomers or a mixture thereof, and wherein one dotted line represents a carbon-carbon single or double bond and the others a carbon-carbon single bond;
each R, independently from each other, represents a hydrogen atom or a methyl or ethyl group provided that at least one of said R groups represents a methyl or ethyl group; and
$R^1$ represents a methyl or ethyl group;
ii) at least one ingredient selected from the group consisting of a perfumery carrier and a perfumery base; and
iii) optionally at least one perfumery adjuvant.

11. A perfuming consumer product comprising:
i) at least one compound of formula (I);

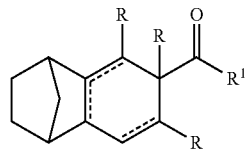

(I)

in the form of any one of its stereoisomers or a mixture thereof, and wherein one dotted line represents a carbon-carbon single or double bond and the others a carbon-carbon single bond;
each R, independently from each other, represents a hydrogen atom or a methyl or ethyl group provided that at least one of said R groups represents a methyl or ethyl group; and
$R^1$ represents a methyl or ethyl group; and
ii) a perfumery consumer base.

12. A perfuming consumer product according to claim 11, wherein the perfumery consumer base is a perfume, a fabric care product, a body-care product, an air care product or a home care product.

13. A perfuming consumer product according to claim 11, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *